(12) United States Patent
Kajimoto et al.

(10) Patent No.: US 8,469,903 B2
(45) Date of Patent: Jun. 25, 2013

(54) ULTRASONIC TREATMENT APPARATUS AND PROGRAM (75) Inventors: Naoko Kajimoto, Mizuho (JP); Kyousuke Kajimoto, Mizuho (JP); Atsumi Ohta, Tokyo (JP); Nobuo Ogiwara, Ageo (JP)

(73) Assignees: Bio Map Co., Ltd., Gifu (JP); Ito Co., Ltd., Tokyo (JP)

( * ) Notice: Subject to any disclaimer, the term of this patent is extended or adjusted under 35 U.S.C. 154(b) by 546 days.

(21) Appl. No.: 12/602,015

(22) PCT Filed: May 15, 2008

(86) PCT No.: PCT/JP2008/058920
§ 371 (c)(1),
(2), (4) Date: Nov. 25, 2009

(87) PCT Pub. No.: WO2008/146609
PCT Pub. Date: Dec. 4, 2008

(65) Prior Publication Data
US 2010/0168623 A1 Jul. 1, 2010

(30) Foreign Application Priority Data
May 29, 2007 (JP) ................................ 2007-142122

(51) Int. Cl.
*A61H 1/00* (2006.01)
(52) U.S. Cl.
USPC .............................................. 601/2; 600/439
(58) Field of Classification Search
USPC .......................................... 601/2–4; 600/439
See application file for complete search history.

(56) References Cited

U.S. PATENT DOCUMENTS 5,413,550 A * 5/1995 Castel ................................ 601/2
5,836,897 A * 11/1998 Sakurai et al. ..................... 601/2
(Continued)

FOREIGN PATENT DOCUMENTS

JP 60-203271 10/1985
JP 8-187265 7/1996
(Continued)

OTHER PUBLICATIONS

Supplementary European Search Report for European Application No. 08752780.0, dated Jun. 8, 2010.
(Continued)

*Primary Examiner* — Unsu Jung
*Assistant Examiner* — Amanda Lauritzen
(74) *Attorney, Agent, or Firm* — Nixon Peabody LLP (57) ABSTRACT

An ultrasonic treatment apparatus according to the present invention includes: an oscillation unit which selectively oscillates a plurality of ultrasonic signals; a data table which includes a plurality of data rows storing in advance frequency data of the ultrasonic signals, at least one data row among the plurality of data rows storing specific frequency data and other frequency data such that a storage amount of the specific frequency data is larger than that of the other frequency data; an operation unit which select one application data row from the plurality of data rows: a plurality of ultrasonic oscillators which include a plurality of resonance frequencies: a plurality of connectors to which the plurality of ultrasonic oscillators are each connectable; a plurality of switches which are each connected, to the plurality of connectors; and a control unit which, in order to apply an application ultrasonic signal selected based on the application data row among the plurality of ultrasonic signals to one application ultrasonic oscillator among the plurality of ultrasonic oscillators, controls the plurality of switches so as to selectively apply the application ultrasonic signal to an application connector connected to the application ultrasonic oscillator, among the plurality of connectors.

17 Claims, 3 Drawing Sheets

U.S. PATENT DOCUMENTS

| | | |
|---|---|---|
| 2001/0039389 A1 | 11/2001 | Sakurai et al. |
| 2003/0181963 A1 | 9/2003 | Pellegrino |
| 2004/0024347 A1 | 2/2004 | Wilson |
| 2005/0070800 A1 | 3/2005 | Takahashi |
| 2006/0206108 A1 | 9/2006 | Hempel |

FOREIGN PATENT DOCUMENTS

| | | |
|---|---|---|
| JP | 11-221290 | 8/1999 |
| JP | 2001-299772 | 10/2001 |
| JP | 2001-520560 | 10/2001 |
| JP | 2001-346805 | 12/2001 |
| JP | 2003-500099 | 1/2003 |
| JP | 2004-528925 | 9/2004 |
| JP | 2004-537383 | 12/2004 |
| JP | 2005-102811 | 4/2005 |
| JP | 2005-230567 | 9/2005 |
| JP | 2006-231053 | 9/2006 |
| WO | 98/47570 | 10/1998 |
| WO | 00/71043 | 11/2000 |
| WO | 02/096506 | 12/2002 |
| WO | 03/013654 | 2/2003 |
| WO | 2004035138 A1 | 4/2004 |
| WO | 2005025403 A2 | 3/2005 |
| WO | 2005107600 A1 | 11/2005 |
| WO | 2006/119572 | 11/2006 |
| WO | 2007/015326 | 2/2007 |

OTHER PUBLICATIONS

International Search Report dated Jun. 16, 2008, for corresponding Patent Application PCT/JP2008/058920.

Office Action for Japanese Application No. 2007-142122, mailed Feb. 14, 2012.

* cited by examiner

ULTRASONIC TREATMENT APPARATUS AND PROGRAM

CROSS-REFERENCE TO RELATED APPLICATIONS

This application is a national stage entry under 35 U.S.C. §371 of PCT Application No. PCT/JP2008/058920 filed 05/15/2008 which claims priority to JP 2007-142122, filed 05/29/2007, all of which are incorporated herein by reference.

TECHNICAL FIELD

The present invention relates to an ultrasonic treatment apparatus which is used to treat bones and soft tissues such as skin and connective tissue, and a program which is executed by a computer of the ultrasonic treatment apparatus.

Priority is claimed on Japanese Patent Application No. 2007-142122, filed May 29, 2007, the content of which is incorporated herein by reference.

BACKGROUND ART

In the past, for the purpose of treating a bone fracture or promoting fixation of an implant to a living body, there was known an ultrasonic treatment apparatus for promoting formation of a new bone tissue by applying ultrasonic vibration to an affected area. In order to regenerate bones, it is necessary to promote the regeneration of soft tissues such as peripheral skin and connective tissue. In the past, there was known a low-frequency treatment apparatus for obtaining a treatment effect by selectively applying a plurality of low frequency vibration to a human body (for example, see Patent Documents 1 and 2).
[Patent Document 1] Japanese Unexamined Patent Application, First Publication No, S60-203271
[Patent Document 2] Japanese Unexamined Patent Application, First Publication No. H11-221290

DISCLOSURE OF INVENTION

Problem to be Solved by the Invention

In the known ultrasonic treatment apparatus, a treatment is performed by changing a treatment time, an ultrasonic output level, or an ultrasonic output timing of the ultrasonic oscillator for applying the ultrasonic vibration to the affected area. For this reason, the treatment was inevitably monotonous, and the careful treatment in accordance with the state of the affected area cannot be performed.

An object of the present invention is to improve the treatment effect by selecting an ultrasonic oscillator from a plurality of ultrasonic oscillators and selecting a frequency of a transmitted ultrasonic signal in accordance with a state of an affected area.

Means for Solving the Problem

An ultrasonic treatment apparatus according to the present invention includes: an oscillation unit which selectively oscillates a plurality of ultrasonic signals having different frequencies; a data table which includes a plurality of data rows storing in advance frequency data of the ultrasonic signals oscillated by the oscillation unit, at least one data row among the plurality of data rows storing specific frequency data and other frequency data such that a storage amount of the specific frequency data is larger than that of the other frequency data; an operation unit which select one application data row from the plurality of data rows; a plurality of ultrasonic oscillators which include a plurality of resonance frequencies corresponding to the plurality of ultrasonic signals and output an ultrasonic wave through an ultrasonic oscillation; a plurality of connectors to which the plurality of ultrasonic oscillators are each connectable; a plurality of switches which are each connected to the plurality of connectors; and a control unit which, in order to apply an application ultrasonic signal selected based on the application data row among the plurality of ultrasonic signals to any one application ultrasonic oscillator among the plurality of ultrasonic oscillators, controls the plurality of switches so as to selectively apply the application ultrasonic signal to an application connector connected to the application ultrasonic oscillator, among the plurality of connectors.

A storage medium according to the present invention stores a program allowing a computer to execute: a storage step of storing in advance a data table in a data unit, the data table including a plurality of data rows for frequency data of an ultrasonic signal oscillated by an oscillation unit, the plurality of data rows storing specific frequency data and other frequency data such mat a storage amount of the specific frequency data is larger than that of the other frequency data; a selection step of selecting one application data row from the plurality of data rows; an oscillation step of selectively oscillating an application ultrasonic signal selected from a plurality of ultrasonic signals having different frequencies based on the application data row; a detection step of detecting a plurality of connection connectors connected to a plurality of ultrasonic oscillators; and a control step of controlling each of a plurality of switches so as to selectively supply the application ultrasonic signal to any one application connector among the plurality of connection connectors.

In the ultrasonic treatment apparatus according to the present invention, the control unit may determine a bone regeneration state of the target treatment portion based on the measurement result, and may control the ultrasonic wave of the plurality of ultrasonic oscillators based on the result.

With the above-described configuration, the ultrasonic wave is irradiated to a bone, and the ultrasonic wave is inspected on the opposite side of the bone with the bone interposed therebetween. In the case where the bone has not been regenerated, the amount of the transmitting ultrasonic wave increases, and hence the ultrasonic wave is more strongly output. In the case where the bone is gradually regenerated, the amount of the transmitting ultrasonic wave decreases, and hence the ultrasonic wave is more weakly output. In addition, even when the ultrasonic wave returning toward the oscillation unit side through the target treatment portion is detected, it is possible to obtain the same effect.

EFFECT OF THE INVENTION

According to the present invention, it is possible to perform the best suitable treatment on an affected area by selectively using a plurality of ultrasonic oscillators. In addition, by means of the configuration in which at least one data row among the plurality of data rows stores the specific frequency data and the other frequency data such that the storage amount of the specific frequency data is larger than that of the other frequency data, it is possible to prevent the effect from deteriorating due to acclimatization to the stimulus. In addition, according to an embodiment of the present invention, when the ultrasonic frequency is changed or the ultrasonic output is controlled in accordance with the parameter inherent in the ultrasonic oscillator, it is possible to perform a more careful treatment in accordance with the state of the affected area. Further, since it is possible to continuously and randomly change the output intensity and the output, it is possible to prevent the acclimatization to the stimulus. Furthermore, according to the embodiment of the present invention, since there is provided a phase difference detecting circuit, it is possible to efficiently drive the ultrasonic oscillator so as to correspond to a variation in resonance frequency due to the individual difference of the ultrasonic oscillator the ambient temperature environment, and the like.

REFERENCE SYMBOLS 1, 2, 3 ULTRASONIC OSCILLATOR
CN1, CN2, CN3 CONNECTOR
S1, S2, S3 SENSOR
EP1, EP2, EP3 MEMORY
4 VCO
5 CPU
6 OUTPUT METHOD SELECTING UNIT
7 FREQUENCY SETTING UNIT
8 GATE CIRCUIT
9 GATE CONTROL SIGNAL
10 DRIVING CIRCUIT
11 WITCHING SIGNAL
12 PHASE DIFFERENCE DETECTING CIRCUIT
14 SELECTION SWITCH
16a, 16b, 16c RESISTOR
20 REFERENCE VOLTAGE CONTROL UNIT
31 PROBE
32 MEMORY
33 CASING
34 CORD
SW1, SW2, SW3 SWITCH

BEST MODE FOR CARRYING OUT THE INVENTION

Hereinafter, an embodiment of the present invention will be described with reference to the drawings.

Figure 1:
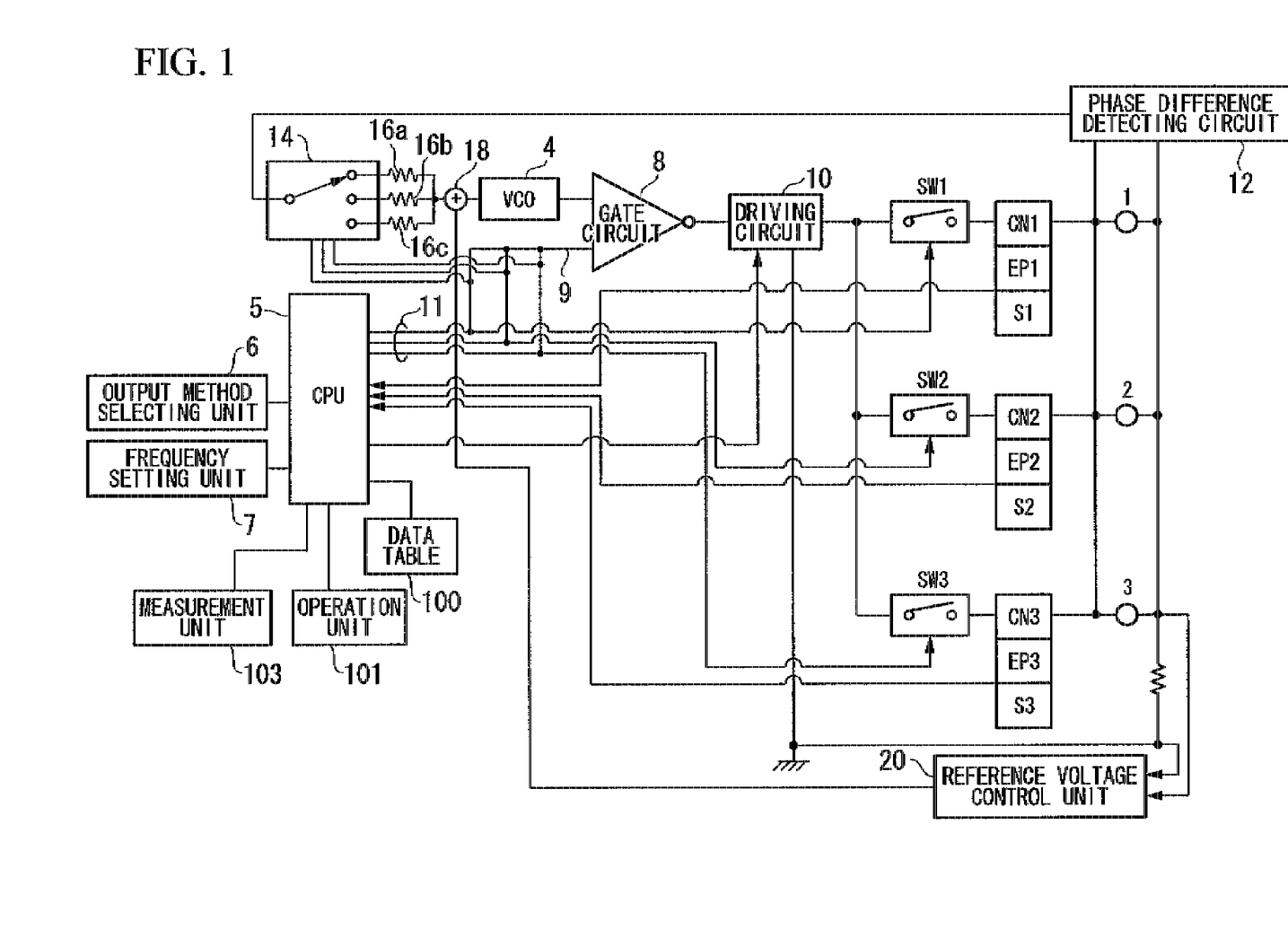
FIG. 1 is a block diagram showing a configuration of an ultrasonic treatment apparatus according to an embodiment of the present invention.

FIG. 1 is a block diagram showing a configuration of an ultrasonic treatment apparatus according to an embodiment of the present invention.

In FIG. 1, an ultrasonic oscillator 1 is connected to a connector CN1 which obtains an ultrasonic output of a channel CH1 (channel 1). An ultrasonic oscillator 2 is connected to a connector CN2 which obtains an ultrasonic output of a channel CH2. An ultrasonic oscillator 3 is connected to a connector CN3 which obtains an ultrasonic output of a channel CHS. The connectors CN1, CN2, and CN3 respectively include sensors (detection portions) S1, S2, and S3 which detect the connection stats of the ultrasonic oscillators 1, 2, and 3, and memories (storage portions) EP1, EP2, and EP3 such as EEPROM (Electrically Erasable Programmable ROM) which store oscillator parameters of the ultrasonic oscillators 1, 2, and 3. The oscillator parameters are, for example, impedance information, a resonance frequency, and the like.

Each of the ultrasonic oscillators 1, 2, and 3 includes a plurality of resonance frequencies (specifically, 5 MHz, 3 MHz, and 1 MHz).

A VCO (Voltage Control Oscillator) 4 is an oscillation unit which oscillates an ultrasonic signal. A CPU (control unit) 5 controls an entire operation of the apparatus. The CPU 5 is connected to an output method selecting unit 6 and a frequency setting unit 7. A gate circuit S gates the oscillation output of the VCO 4 by means of a gate signal 9 obtained from the CPU 5. A driving circuit 10 amplifies an ultrasonic signal through the gate circuit 8. Switches SW1, SW2, and SW3 selectively supply the amplified ultrasonic signals to the connectors CN1, CN2, and CN3, and are selectively controlled by a switching signal 11 obtained from the CPU 5. That is, the CPU 5 controls the switches to be turned on so that the ultrasonic wave is transmitted to a connector (application connector) connected to the ultrasonic oscillator (application ultrasonic oscillator) to which, the ultrasonic signal is supplied. On the other hand, the CPU 5 controls the other switches to be turned off. At this time, in addition, the CPU 5 controls the switches SW1, SW2, and SW3 so that the ultrasonic signal is transmitted to the connector (connection connector) connected to the ultrasonic oscillator. On the other hand, the CPU 5 controls the switches SW1, SW2, and SW3 so mat the ultrasonic signal is not transmitted to the connector not connected to the ultrasonic oscillator. The driving circuit 10 may be configured so that its output is controlled by the CPU 5.

Each of the switches SW1, SW2, and SW3 includes a transistor or an FET (Field-Effect Transistor). The gate signal 9 is a signal obtained by adding the switching signals 11, output from the CPU 5 to each of the switches SW1, SW2, and SW3, to each other.

The outputs obtained from each of the connectors CN1, CN2, and CN3 and each of the driving signal outputted via the ultrasonic oscillators 1, 2, and 3 are input to the phase difference detecting circuit 12.

A selection switch 14 is selectively controlled in synchronization with the switches SW1, SW2, and SW3 by the CPU 5.

Resistors 16a, 16b, and 16c have resistance values determined in accordance with the used frequencies of the ultrasonic oscillators 1, 2, and 3. Specifically, the resistor 16a hag a resistance value corresponding to a resonance frequency of 5 MHz. The resistor 16b has a resistance value corresponding to a resonance frequency of 3 MHz. The resistor 16c has a resistance value corresponding to a resonance frequency of 1 MHz.

For example, a case will be described In which an ultrasonic wave of 5 MHz is output from any one of the ultrasonic oscillators 1, 2, and 3. In this case, the CPU 5 controls the selection switch 14 to he connected to the resistor 16a.

As shown in FIG. 1, an adder 18 is connected to the resistors 16a, 16b, and 16c, the VCO 4, and a reference voltage control unit 20. Immediately after the switches SW1, SW2, and SW3 are changed by the CPU 5, the reference voltage control unit 20 controls a reference voltage supplied through the adder 18 to the VCO 4 as the oscillation unit for oscillating the corresponding ultrasonic oscillators 1, 2, and 3.

For example, the ultrasonic oscillators 1, 2, and 3 are respectively connected to the connectors CN1, CN2, and CN3. A case will be described in which an ultrasonic wave of 5 MHz is oscillated by any one of the ultrasonic oscillators 1, 2, and 3. Here, the ultrasonic oscillator 1 is selected. In this case, the CPU 5 performs a control so that an ultrasonic signal is applied to the ultrasonic oscillator 1 (application ultrasonic oscillator). That is, the CPU 5 performs a control so mat an ultrasonic signal is applied to the connector CN1 (application connector) connected to the ultrasonic oscillator 1 (application ultrasonic oscillator). Accordingly, the CPU 5 controls the switch SW1 to be turned on. On the other hand, the CPU 5 controls the switches SW2 and SW3 to be turned off. Based on the ON state of the switch SW1, a voltage for outputting an ultrasonic signal of 5 MHz is applied from the reference voltage control unit 20 to the VCO 4. Accordingly, the ultrasonic signal is applied to the connector CN1, and the ultrasonic signal is applied to the ultrasonic oscillator 1 through the connector CN1. As a result, the ultrasonic wave of 5 MHz is output from the ultrasonic oscillator 1.

Figure 3:
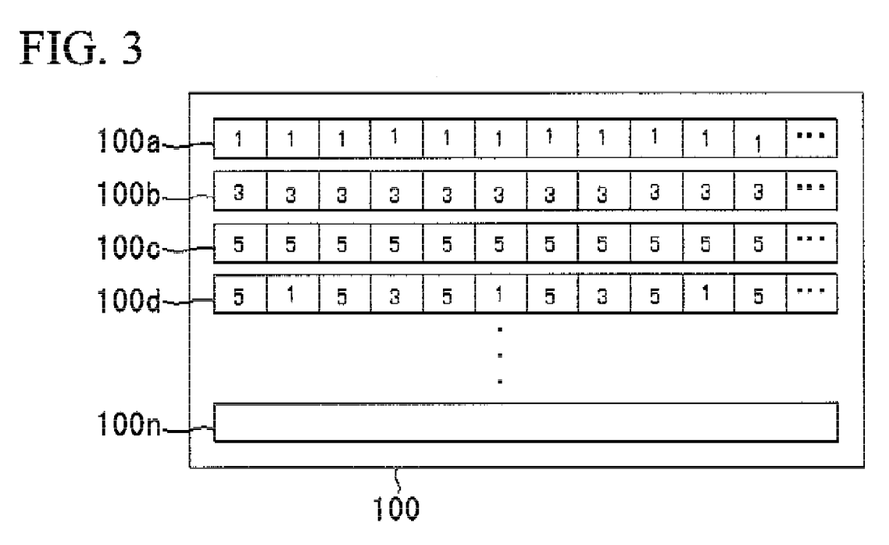
FIG. 3 is a diagram showing a configuration of a data table of the ultrasonic treatment apparatus according to the embodiment of the present invention shown in FIG. 1.

FIG. 3 shows a configuration of a data table (data unit) 100. The data table 100 is a memory. The data table 100 includes a plurality of data rows 100a to 100n storing in advance the frequency data of the ultrasonic signal oscillated by the oscillation unit. As shown in FIG. 1, the CPU 5 is connected to the data table 100 and an operation unit 101. The operation unit 101 selects one data row (application data row) from a plurality of data rows 100a to 100n of the data table 100. The CPU 5 controls the oscillation frequency of the oscillation unit based on the frequency data stored in the data row (application data row) selected by the operation unit 101.

One data row 100d of a plurality of data rows 100a to 100n stores the specific frequency data and other frequency data. In addition, in the data row 100d, a storage amount of the specific frequency data is larger than mat of the other frequency data. For example, assuming that the specific frequency is 5 MHz and the other frequencies are 1 MHz and 3 MHz, the following data row is obtained.

Data row 100d: 5, 1, 5, 3, 5, 1, 5, 3, 5, 1, 5, 3, 5 . . .

Based on the data row 100d, an example will be described in which the ultrasonic wave is output from the ultrasonic treatment apparatus. The ultrasonic oscillators 1, 2, and 3 are respectively connected to the connectors CN1, CN2, and CN3. At the first location of the data row 100d, 5 MHz is set. For this reason, the CPU 5 performs a control so that the ultrasonic signal is applied to any one ultrasonic oscillator (application ultrasonic oscillator) among the ultrasonic oscillators 1, 2, and 3. That is, it is controlled so that the ultrasonic signal is applied to the application connector connected to the application ultrasonic oscillator. Here, the ultrasonic oscillator 2 is selected. Accordingly, the CPU 5 performs a control so that the ultrasonic signal is applied to the connector CN2. That is, the CPU 5 controls the switch SW2 to be turned on. On the other hand, the CPU 5 controls the switches SW1 and SW3 to be turned off. Based on the ON state of the switch SW2, a voltage for outputting an ultrasonic signal of 5 MHz is applied from the reference voltage control unit 20 to the VCO 4. Accordingly, the ultrasonic signal is applied to the connector CN2, and the ultrasonic signal is applied to the ultrasonic oscillator 2 through the connector CN2. As a result, the ultrasonic wave of 5 MHz is output from the ultrasonic oscillator 2. After a predetermined time has elapsed, 1 MHz set at the second location of the data row 100d is output. For this reason, the CPU 5 performs a control so that the ultrasonic signal is applied to any one ultrasonic oscillator among the ultrasonic oscillators 1, 2, and 3. Here, the ultrasonic oscillator 3 is selected. In this case, the CPU 5 performs a control so that the ultrasonic signal is applied to the connector CN3. For this reason, the CPU 5 controls the switch SW3 to be turned on, and controls the switches SW1 and SW2 to be turned off. Based on the ON state of the switch SW3, a voltage for outputting an ultrasonic signal of 1 MHz is applied from the reference voltage control unit 20 to the VCO 4. Accordingly, the ultrasonic signal is applied to the connector CN3, and the ultrasonic signal is applied to the ultrasonic oscillator 3 through the connector CN3. As a result the ultrasonic oscillator 3 is oscillated, and outputs an ultrasonic wave of 1 MHz. Then, the same routine as described above is repeated so as to output the frequencies stored in the data row 100d.

In the same manner as the above-described example, in the case where the application ultrasonic signals selected based on the application data row are sequentially output, in every data set in the application data row, any one ultrasonic oscillator (application ultrasonic oscillator) is selected from the ultrasonic oscillators connected to the connectors. At this time, for example, in all cases, only the ultrasonic oscillator 1 may be used, the ultrasonic oscillators 1, 2, and 3 may be sequentially used, or the ultrasonic oscillators 1, 2, and 3 may be randomly used.

The data of the data row may be made as below. First, a plurality of data rows 100a to 100n are expanded. The expanded data row stores an output data of an ultrasonic signal and a duty ratio data of an ultrasonic signal as a square-wave signal in addition to the frequency data of the ultrasonic signal oscillated by the oscillation unit. In response to this, the output of the ultrasonic signal and the duty ratio of the square-wave signal input to the oscillation unit are changed together with the frequency of the ultrasonic signal oscillated by the oscillation unit. At this time, an integral value per hour of the irradiation energy may be set in advance, and the output and the duty ratio may be controlled so that the range is uniform in the case of the same frequency. For example, the range is as below.

Data row (frequency, duty ratio, and output): (5, 0.5, 0.125), (1, 0.5, 0.25), (5, 0.25, 0.25), (3, 0.5, 0.125), (5, 0.125, 0.5), . . .

Next, an operation according to the above-described configuration will be described.

Figure 2:
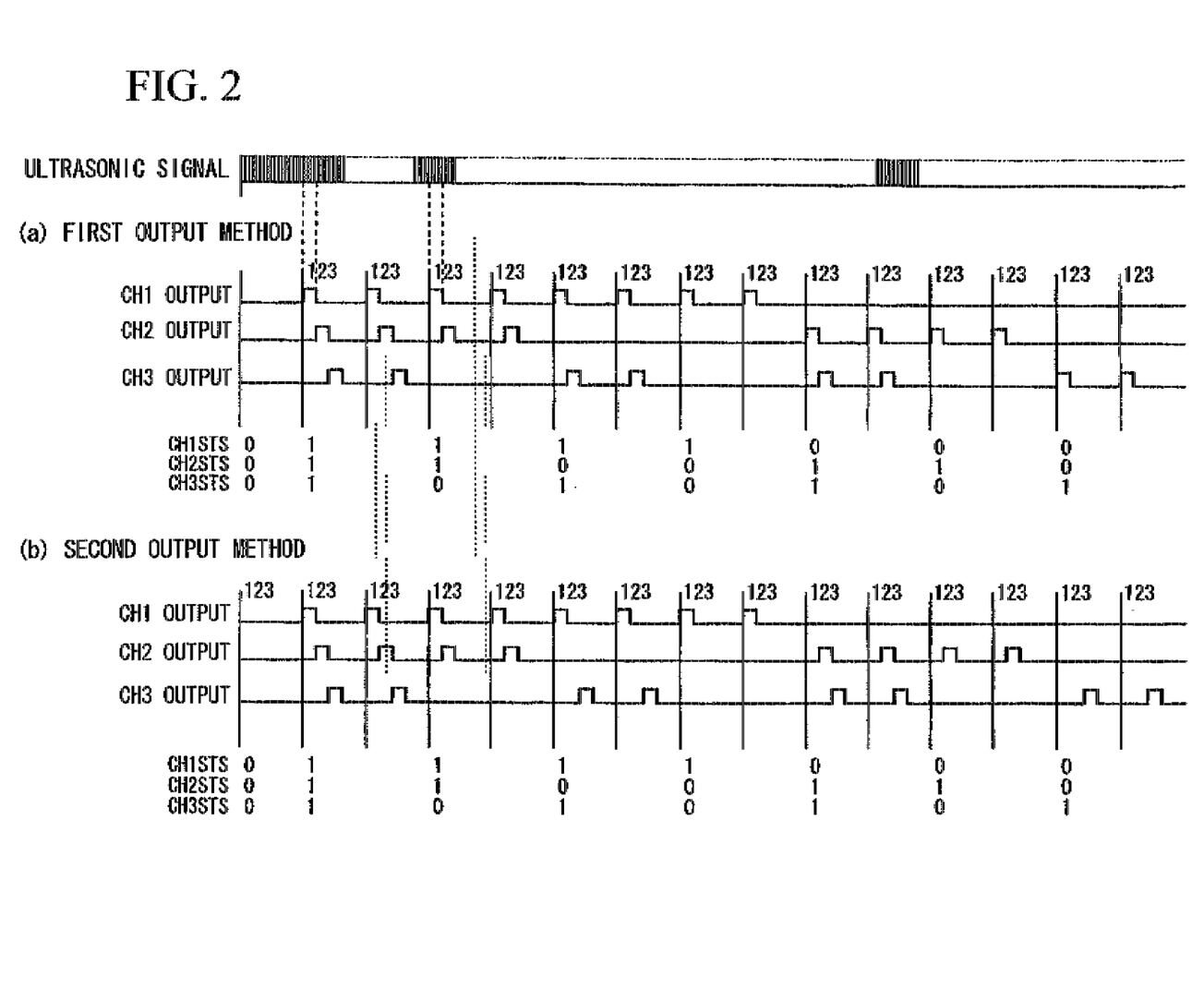
FIG. 2 is a timing chart showing an ultrasonic output timing of each of CH1, CH2, and CH3 of the ultrasonic treatment apparatus according to the embodiment of the present invention shown in FIG. 1.

The CPU 5 outputs the gate signal 9 for controlling the gate circuit 8 in accordance with the detection of the sensors S1, S2, and S3. Moreover, the CPU 5 outputs the switching signal 11 for controlling the switches SW1, SW2, and SW3 and the selection switch 14. In accordance with the control signal (the gate signal 9 and the switching signal 11), as shown in FIG. 2, a plurality of (in FIG. 2, eight) output patterns of the ultrasonic outputs of the channels CH1, CH2, and CH3 output from the connectors CN1, CN2, and CN3 axe obtained. FIG. 2(a) shows an example of a first output method, and FIG. 2(b) shows an example of a second output method. The first or second output method is selected by the output method selecting unit 6.

In FIG. 2, each of the pulses shown in the channels CH1, CH2, and CH3 is the gate signal 9 or the switching signal 11 for extracting the ultrasonic signal. There are eight combinations in which the ultrasonic oscillators 1, 2, and 3 are connected to the connectors CN1, CN2, and CN3, and the combinations are indicated by the status STS of three bits such as "000" and "111". In accordance with the status STS, the ultrasonic signal output timing is automatically changed. There is no output in the case where the status STS is 0.

In the case of the first output method shown in FIG. 2(a), the output timings of the channels CH1, CH2, and CH3 are sequentially adjacent to each other regardless of the status STS. For example, in the case of "111", the pulses of three channels CH1, CH2, and CH3 are sequentially adjacent to each other. In the case of "101", the pulses of channels CH1 and CHS are adjacent to each other. Likewise, a portion without the pulse is filled with other pulses, and is output. Next, the second output method shown in FIG 2(b) will be described. In the case of "111", the pulses of three channels CH1, CH2, and CH3 are sequentially adjacent to each other. In the case of "101", a portion between the channels CH1 and CH3 is not filled, but is empty by an amount corresponding to the pulse of the channel CH2.

FIGS. 2(a) and 2(b) show an example of the output timing pattern. In addition, the pulse position, the pulse width, and the like for each of the channels CH1, CH2, and CH3 may be modified.

As described above, the CPU 5 outputs the gate signal 9 and the switching signal 11. In addition, the CPU 5 reads the oscillator parameters of the ultrasonic oscillators 1, 2, and 3 stored in the memories EP1, EP2, and EP3 which are built-in the connectors CN1, CN2, and CN3. The CPU 5 controls the VCO 4 so that the ultrasonic signal is output in accordance with the read parameters. That is, it is controlled so that the ultrasonic signals are output in accordance with the impedance information, the resonance frequency, and the like which are inherent in each of the ultrasonic oscillators 1, 2, and 3 during a period of the pulses of the channels CH1, CH2, and CH3 (a period in which the switches SW1, SW2, and SW3 are turned on).

The output of the VCO 4 is supplied to the ultrasonic oscillators 1, 2, and 3 through the gate circuit 8, the driving circuit 10, and the switches SW1, SW2, and SW3, and the ultrasonic oscillators 1, 2, and 3 are oscillated to output an ultrasonic wave in accordance with the selection state of the switches SW1, SW2, and SW3.

In the embodiment, three ultrasonic oscillators are used, but two or three or more ultrasonic oscillators may be used. The gate circuit 8 for controlling the oscillation output timing may be omitted.

Next, a feedback circuit for matching the oscillation frequency of the VCO 4 with the resonance frequency of each of the ultrasonic oscillators 1, 2, and 3, which is changed in accordance with, for example, the ambient environment temperature, will be described.

A phase difference between the output of the VCO 4 input to the ultrasonic oscillators 1, 2, and 3 through the switches SW1, SW2, and SW3 and the signal output from the ultrasonic oscillators 1, 2, and 3 is supplied to the phase difference detecting circuit 12. The phase difference detecting circuit 12 includes, for example, a lock-in amp 12.

The phase difference detection output from the phase difference detecting circuit 10 is input to the adder 18 through the selection switch 14, and the resistors 16a, 16b, and 16c. Combination of the selection switch 14 and the resistors 16a, 16b, and 16c is called a variable frequency changing unit. As described above, the resistors 16a, 16b, and 16c have resistance values, which are appropriately set for setting the frequency variable range of the VCO 4 corresponding to the resonance frequencies of the ultrasonic oscillators 1, 2, and 3. The resistors 16a, 16b, and 16c generate an adjustment voltage to be input to the adder 18 based on the potential difference corresponding to the phase difference detected by the phase difference detecting circuit 12. The adjustment voltage and the reference voltage generated by the reference voltage control unit 20 are added by the adder 18, and the resultant is input to the VCO 4. By performing adjustment of the oscillation frequency output from the VCO 4 by the adjustment voltage, the VCO 4 matches the oscillation frequency of the VCO 4 with the resonance frequency of each of the ultrasonic oscillators 1, 2, and 3.

According to the embodiment described above, a plurality of (in this embodiment, three) connectors are provided so as to be each connected to the ultrasonic oscillators. In addition, in accordance with the connection state of the ultrasonic oscillator, the ultrasonic signal is supplied to the connection ultrasonic oscillator at a predetermined output timing every predetermined period. For this reason, since it is possible to selectively use a plurality of ultrasonic oscillators, it is possible to perform the best suitable treatment on the affected area.

By changing the ultrasonic frequency, it is possible to realize a multiple frequency output by using one ultrasonic treatment apparatus. For this reason, since it is possible to select the frequency in accordance with the state of the affected area, it is possible to perform a very careful treatment. In addition, it is possible to control the ultrasonic output in accordance with the parameters inherent in the ultrasonic oscillators. For this reason, since it is possible to perform more careful ultrasonic treatment, a remarkably excellent treatment effect can be obtained compared to the known ultrasonic treatment apparatus.

Next, a program and a storage medium storing the program according to the embodiment will be described.

In a computer system, a program according to the embodiment of the present invention executed by the CPU 5 is performed based on the above-described operation of the ultrasonic treatment apparatus according to the embodiment.

As a storage medium for storing the program, an optical magnetic disk, an optical disk, a semiconductor memory, a magnetic storing medium, or the like may be used, and they may be used by configuring them in a ROM, a RAM, a CD-ROM, a flexible disk, a memory card, or the like.

An example of the storage medium includes a storage medium storing a program for a predetermined time. For example, the storage medium is a volatile memory such as a RAM inside a computer system becoming a server or a client in the case where the program is transmitted through a telecommunication line such as a telephone communication or a network such as the internet.

The program may be transmitted from the computer system storing the program in a storage device or the like to another computer system through a transmission medium or a transmission wave of the transmission medium. The transmission medium indicates a medium having a function of transmitting information like a telecommunication line (communication line) such as a telephone line or a network (communication network) such as the internet.

The program may perform a part of the above-described functions. In addition, it may also be a program that enables implementation of the above-described functions in combination with a program already recorded in the computer system, so-called differential file (differential program).

Accordingly, even when tie program and the storing medium are used in a system or apparatus different from the system or apparatus shown in FIG. 1, and the program is executed by a computer of the system or apparatus, it is possible to obtain similar function and effect as those of the embodiment, and to achieve the object of the present invention.

Next, an example of the treatment will be described.

In the case where an ultrasonic wave is irradiated to a living body, a reaching depth is different in accordance with the frequency thereof. In the case of the ultrasonic treatment apparatus capable of outputting the ultrasonic waves of 1

MHz, 3 MHz, and 5 MHz from the ultrasonic oscillator, when an affected area is a surface portion, a data row having the longest irradiation time of the ultrasonic wave of 5 MHz among the total irradiation time of the ultrasonic waves of 1 MHz, 3 MHz, and 5 MHz is selected from the data rows 100a to 100n of the data table 100, and the ultrasonic wave is irradiated. In the same manner, when a data row having the longest irradiation time of the ultrasonic wave of 1 MHz for the deepest portion or the ultrasonic wave of 3 MHz for the middle portion among the total irradiation time of the ultrasonic waves is selected from the data rows 100a to 100n of the data table 100, and the ultrasonic wave is irradiated, it is possible to perform a very effective treatment. Accordingly, when a ratio between the irradiation time of the ultrasonic wave of 1 MHz, 3 MHz, or 5 MHz and the total irradiation time of the ultrasonic waves is changed, it is possible to allow the stimulus of the ultrasonic wave to reach any target portion in the living body. In addition, since the frequency is changed to three frequencies of 1 MHz, 3 MHz, and 5 MHz during the irradiation time of the ultrasonic wave, it is difficult to decrease the stimulus acclimatization threshold value of the living body.

Instead of the operation unit 101, the CPU 5 may automatically select a different data row every predetermined time so that the ultrasonic wave according to the data row is irradiated for a predetermined time. According to this method, it is more difficult to decrease the stimulus acclimatization threshold value of the living body. The selection method may be random. At this time, the integral value of the irradiation energy per hour may be set in advance, and the output and the duty ratio during the irradiation time may be appropriately controlled so that the range is uniform.

Figure 4:
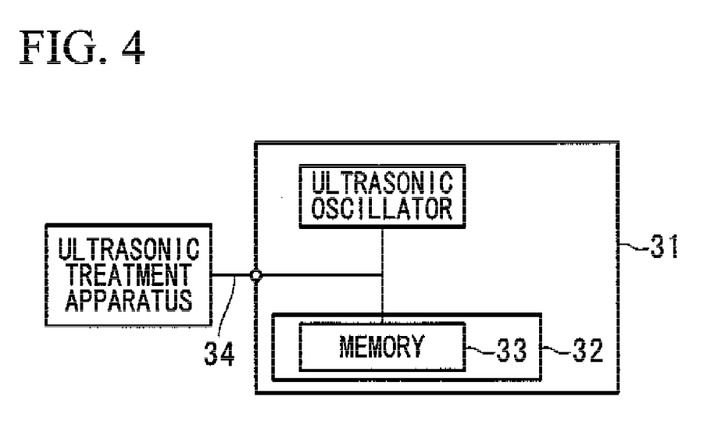
FIG. 4 is a block diagram showing a configuration of a probe of the ultrasonic treatment apparatus according to the embodiment of the present invention shown in FIG. 1.

As shown in FIG 4, a probe 31 including the ultrasonic oscillators 1, 2, and 3 may have a memory 32 for storing the operating time of the probe 31. In FIG 4, the probe 31 includes the ultrasonic oscillators 1, 2, and 3, the memory 32 which stores the operating time, a casing 33 which accommodates the ultrasonic oscillators 1, 2, and 3 and the memory 32, and a cord 34 which is used to be connected to the ultrasonic treatment apparatus. The CPU 5 rewrites the data of the memory 32 in accordance with the time of the probe 31 having been operated while the probe 31 is connected to the ultrasonic treatment apparatus. In this configuration, when the CPU 5 determines that the operating time of the probe 31 stored in the data reaches a predetermined operating time at a time when rewriting the data and reading the data of the memory 32, the ultrasonic treatment apparatus may inform the exchange (life span) of the probe 31 through appropriate means.

In addition, in the case where the probe 31 is exclusively used for a particular patient, the CPU 5 may use the operating time of the probe 31 stored in the data of the memory 32, through appropriate means, for the purpose of treating the patient.

In addition, the ultrasonic treatment apparatus may include a measurement unit 103 shown in FIG. 2. The measurement unit 103 measures the transmission or reflection of the ultrasonic wave irradiated from the ultrasonic treatment apparatus to the target treatment portion. The CPU 5 (control unit) determines the bone regeneration state of the target treatment portion based on the measurement result of the measurement unit, and controls the output of the ultrasonic treatment apparatus based on the result.

After the ultrasonic wave is irradiated onto the bone, the measurement unit 103 inspects the ultrasonic wave on the opposite side of the bone with the bone interposed therebetween. In the case where the bone has not regenerated, the amount of the transmitting ultrasonic waves increases. In this case, the CPU 5 may perform a control so that the ultrasonic waves are more strongly output. In the case where the bone is gradually regenerated, the amount of the transmitting ultrasonic waves decreases. In this case, the CPU 5 may perform a control so that the ultrasonic waves are more weakly output. Even when an ultrasonic wave returning toward the oscillation unit side through the target treatment portion is detected, it is possible to obtain the same effect.

As described above, the ultrasonic treatment apparatus according to the embodiment is capable of outputting three types or more of frequencies (1 MHz, 3 MHz, and 5 MHz), has a variation of three types or more of output magnitude (0.5, 0.25, and 0.125), and is capable of outputting three types or more of pulse shapes (duty ratio: 0.5, 0.25, and 0.125). For this reason, it is possible to more carefully apply the stimulus to the target treatment portion. In addition, since it is possible to more carefully apply the stimulus, it is possible not only to regenerate bones but also to promote regeneration of soft tissues such as peripheral skin and connective tissue, and from the comprehensive or steric viewpoint, it is remarkably effective in the regeneration of the bone.

INDUSTRIAL APPLICABILITY

The present invention may be applied to the ultrasonic treatment apparatus which is used to treat bones and soft tissues such as skin and connective tissue. According to the ultrasonic treatment apparatus, when a plurality of ultrasonic oscillators are selectively changed in accordance with the state of the affected area and the frequencies of the irradiated ultrasonic signal are selectively changed, it is possible to improve the treatment effect.

The invention claimed is:
1. An ultrasonic treatment apparatus comprising:
an oscillator configured to selectively oscillate a plurality of ultrasonic signals having different frequencies;
a memory configured to contain a data table which includes a plurality of data rows storing in advance frequency data of the ultrasonic signals oscillated by the oscillator, at least one data row among the plurality of data rows storing specific frequency data and other frequency data such that a storage amount of the specific frequency data is larger than that of the other frequency data;
a central processing unit (CPU) configured to select one application data row from the plurality of data rows;
a plurality of ultrasonic oscillators configured to include a plurality of resonance frequencies corresponding to the plurality of ultrasonic signals and output an ultrasonic wave through an ultrasonic oscillation;
a plurality of connectors configured to be connected to the plurality of ultrasonic oscillators respectively;
a plurality of switches configured to be each connected to the plurality of connectors; and
the CPU, in order to apply an application ultrasonic signal selected based on the application data row among the plurality of ultrasonic signals to any one application ultrasonic oscillator among the plurality of ultrasonic oscillators, configured to control the plurality of switches so as to selectively apply the application ultrasonic signal to an application connector connected to the application ultrasonic oscillator, among the plurality of connectors.

2. The ultrasonic treatment apparatus according to claim 1, further comprising:
a sensor configured to detect a connection connector connected to the plurality of ultrasonic oscillators, among the plurality of connectors,
wherein the CPU is configured to control each of the plurality of switches so as to supply the application ultrasonic wave to only the connection connector.

3. The ultrasonic treatment apparatus according to claim 2, wherein a memory configured to store an oscillator parameter of each of the plurality of ultrasonic oscillators is provided, and the CPU is configured to read, from the memory, the oscillator parameter of the ultrasonic oscillator connected to the connection connector, among the plurality of ultrasonic oscillators and control an oscillation output of the oscillator based on the read oscillation parameter.

4. The ultrasonic treatment apparatus according to claim 3, wherein the memory is provided for each of the plurality of connectors.

5. The ultrasonic treatment apparatus according to claim 1, further comprising:
a phase difference detecting circuit configured to detect a phase difference between an oscillation frequency of the oscillator and a signal output through the plurality of ultrasonic oscillators and output a phase difference detection result,
wherein the oscillation frequency of the oscillator is configured to be controlled based on the phase difference detection result.

6. The ultrasonic treatment apparatus according to claim 5, further comprising:
a variable frequency changing circuit configured to change a variable range of the oscillation frequency of the oscillator so as to correspond to each of the ultrasonic oscillators.

7. The ultrasonic treatment apparatus according to claim 1, wherein the CPU is configured to supply to the application connectors respectively at different timings every predetermined period.

8. The ultrasonic treatment apparatus according to claim 1, wherein the CPU is configured to select a different application data row for the application connector every predetermined period.

9. The ultrasonic treatment apparatus according to claim 1, further comprising:
a reference voltage controller configured to supply a reference voltage in accordance with the application ultrasonic signal to the oscillator based on control of the plurality of switches by the CPU.

10. The ultrasonic treatment apparatus according to claim 1, further comprising:
a measurement sensor configured to measure transmission or reflection of the ultrasonic wave irradiated from the plurality of ultrasonic oscillators to a target treatment portion and output the measurement result,
wherein the CPU is configured to determine a bone regeneration state of the target treatment portion based on the measurement result, and control the ultrasonic wave of the plurality of ultrasonic oscillators based on the result.

11. The ultrasonic treatment apparatus according to claim 1, wherein the CPU is configured to randomly change an amount of the ultrasonic wave irradiated onto a target treatment portion.

12. The ultrasonic treatment apparatus according to claim 1, wherein the CPU is configured to randomly change intermittence of the ultrasonic wave irradiated onto a target treatment portion.

13. The ultrasonic treatment apparatus according to claim 1, further comprising:
a probe configured to include a memory storing an operating time and the plurality of ultrasonic oscillators,
wherein the CPU is configured to rewrite data in the memory in accordance with a time of the plurality of ultrasonic oscillators having been operated.

14. A non-transitory storage medium comprising: a program causing a computer to execute:
storing in advance a data table in a data unit, the data table including a plurality of data rows for frequency data of an ultrasonic signal oscillated by an oscillator, the plurality of data rows storing specific frequency data and other frequency data such that a storage amount of the specific frequency data is larger than that of the other frequency data;
selecting one application data row from the plurality of data rows;
selectively oscillating an application ultrasonic signal selected from a plurality of ultrasonic signals having different frequencies based on the application data row;
detecting a plurality of connection connectors connected to a plurality of ultrasonic oscillators; and
controlling each of a plurality of switches so as to selectively supply the application ultrasonic signal to any one application connector among the plurality of connection connectors.

15. The storage medium according to claim 14, wherein the plurality of ultrasonic signals are supplied to the application connectors respectively at different timings every predetermined period.

16. The storage medium according to claim 14, wherein a different data row is selected for the application connector every predetermined period.

17. The storage medium according to claim 14, wherein from a storage medium storing an oscillator parameter of each of the plurality of ultrasonic oscillators connected to the plurality of connection connectors, the oscillator parameter is read, and the selectively oscillating is controlled based on the read oscillator parameter.

* * * * *

UNITED STATES PATENT AND TRADEMARK OFFICE
CERTIFICATE OF CORRECTION

PATENT NO. : 8,469,903 B2  
APPLICATION NO. : 12/602015  
DATED : June 25, 2013  
INVENTOR(S) : Kajimoto et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 580 days.

Signed and Sealed this
Eighth Day of September, 2015

Michelle K. Lee
*Director of the United States Patent and Trademark Office*